United States Patent [19]

Reed

[11] Patent Number: 4,489,446

[45] Date of Patent: Dec. 25, 1984

[54] HEART VALVE PROSTHESIS

[76] Inventor: Charles C. Reed, 5934 Hornwood, Houston, Tex. 77071

[21] Appl. No.: 398,084

[22] Filed: Jul. 14, 1982

[51] Int. Cl.$^3$ .............................................. A61F 1/22
[52] U.S. Cl. ......................................... 3/1.5; 137/846
[58] Field of Search ....................... 137/846, 852, 516; 3/1.5

[56] References Cited

U.S. PATENT DOCUMENTS

| | | | |
|---|---|---|---|
| 3,508,281 | 4/1970 | Cromie | 3/1 |
| 3,534,411 | 10/1970 | Shiley | 3/1 |
| 3,656,185 | 4/1972 | Carpentier | 3/1 |
| 3,714,671 | 2/1973 | Edwards et al. | 3/1 |
| 3,898,999 | 8/1975 | Haller | 3/1.5 |
| 4,042,979 | 8/1977 | Angell | 3/1.5 |
| 4,055,861 | 11/1976 | Carpentier et al. | 3/1.5 |

OTHER PUBLICATIONS

A. Carpentier et al., "A New Reconstructive Operation for Correction of Mitral and Tricuspid Insufficiency", 61 *Journal of Thoracic & Cardiovascular Surgery*, (No. 1), 1–13, (Jan. 1971).

Denton A. Cooley et al., "Replacement and/or Repair of the Mitral Valve as Treatment of Idiopathic Hypertrophic Subaortic Stenosis", 3 *Cardiovascular Diseases, Bulletin of the Texas Heart Institute*, (No. 4), 381–393, (1976).

Denton A. Cooley et al., "Mitral Leaflet Prolapse: Surgical Treatment Using a Posterior Annular Collar Prosthesis", 3 *Cardiovascular Diseases, Bulletin of the Texas Institute*, (No. 4), 438–443, (1976).

Carlos D. Duran and Jose Luis M. Ubago, "Clinical and Hemodymanic Performance of a Totally Flexible Prosthetic Ring for Atrioventricular Valve Reconstruction", 5 *Annals of Thoracic Surgery*, (No. 5), 458–463, (Nov. 1976).

M. Puig Massana et al., "Conservative Surgery of the Mitral Valve Annuloplasty on a New Adjustable Ring", *Cardiovascular Surgery* 1980, 30–37, (1981).

*Primary Examiner*—Richard J. Apley
*Assistant Examiner*—D. J. Isabella
*Attorney, Agent, or Firm*—Workman, Nydegger & Jensen

[57] ABSTRACT

A heart valve prosthesis incorporating a dynamic stiffener element is disclosed. The prosthesis is adapted for securement to the annulus of an atrioventricular valve and has the characteristic of allowing normal movement of the annulus during the cardiac cycle while providing mechanical support to the valve annulus so as to maintain the valve leaflets in proper physiological alignment. The stiffener element has a plurality of reciprocating members allowing it to be modifiable in shape so as to be capable of assuming the optimum shape for a particular heart valve.

14 Claims, 11 Drawing Figures

HEART VALVE PROSTHESIS

BACKGROUND

1. Field of the Invention

The present invention relates to an improved heart valve prosthesis for use in the surgical repair of atrioventricular heart valves.

2. The Prior Art

The mitral and triscuspid valves are located in the atrioventricular openings of the heart and serve to prevent regurgitation of blood from the ventricle into the atrium when the ventricle contracts. The mitral valve is located in the left atrioventricular opening of the heart. It is encircled by a dense fibrous ring known as the annulus and consists of two valve cusps or leaflets. These two leaflets are of unequal size. The anterior leaflet, being situated adjacent to the aortic opening, is often called the ventral, anterior, or aortic cusp. The smaller posterior leaflet is known as the dorsal or posterior cusp. The leaflets are composed of strong fibrous tissue which is thick in the central part but thin and translucent near the margin. They are held in place by chordae tendinae and papillary muslces. The line at which the leaflets come together is called a commissure.

The tricuspid valve is located in the right atrioventricular opening and comprises three leaflets, sometimes referred to as the anterior, posterior, and septal cusps. These leaflets are roughly triangular in shape and are also attached to a fibrous ring.

The mitral valve is subjected to significantly higher back pressure than is the tricuspid valve. Accordingly, it is far more common to require surgery to repair a mitral valve than for a tricuspid valve.

Normal function of the mitral valve requires the coordinated interaction of six anatomic elements: the leaflets, chordae tendinae, annulus, the left atrium, the papillary muscles and the left ventricular wall. The most common defect leading to mitral dysfunction is a dilatation or elongation of the posterior two-thirds of the annulus, the section corresponding to the posterior leaflet. The anterior portion of the annulus is anchored to the aortic root and is thus not as subject to elongation. However, not infrequently in cases of mitral valve dysfunction the anterior leaflet is displaced away from the center of the valve and is slightly thickened and shortened. Thus, in repairing a mitral valve, it is sometimes necessary to reduce the annulus in its physiological dimensions by repairing the dilatated posterior two-thirds thereof. Also, it is generally necessary to restore the commissure to its normal physiological curvature. Also, it is often necessary to reposition and reshape the anterior leaflet to correct any malposition and shortening of tissue which may have occurred.

Although the discussion above has been directed specifically towards the mitral valve, similar concepts apply to the correction of tricuspid valve defects.

One solution to serious valve dysfunction is total valve replacement. However, it is generally agreed that repair of the valve by techniques of annuloplasty are preferable to valve replacement. One valve prosthesis is described in U.S. Pat. No. 3,656,185 to Carpentier. This prosthesis consists of a rigid annular or part-annular member adapted to fit against the base of the valve leaflets and secured in place by sutures. Although this device constituted a significant advancement in the treatment of mitral valve dysfunction, because of its rigidity it did not allow natural movement of the annulus during the cardiac cycle. In a normal heart, there are continuous changes of the mitral and tricuspid annuli during the cardiac cycle. When a rigid ring of the type utilized by Carpentier is utilized, the annulus is not permitted to undergo these changes. Another disadvantage with the rigid ring is the tendency for the securement sutures to be torn loose from the annulus as the result of stress caused by restraining the annulus from undergoing normal physiological changes during the cardiac cycle.

Thus, Duran and Ubago considered it desirable to construct a flexible ring for use in atrioventricular annuloplasty so as to accommodate and follow the movements of the annulus during the cardiac cycle. It was their belief that in addition to the obvious advantage of allowing the heart to function in a more natural manner, use of a flexible ring would also decrease the chance of having the ring become partially detached from the annulus, because the stress forces on any particular point along the ring are reduced. Thus, Duran and Ubago developed a totally flexible prosthetic ring. Their initial results are reported in The Annals of Thoracic Surgery, Volume 22, No. 5, November 1976.

Subsequently, Massana improved upon the totally flexible ring by the addition of a traction thread which is passed through the interior of the ring, with both ends exiting the ring a short distance apart. Once implanted, the ring can be reduced in size, together with the annulus, by pulling on the traction threads until the valve becomes competent in a manner very similar to pulling a pair of purse strings. The ring may be contracted symmetrically by pulling both ends of the traction thread the same amount, or the ring may be contracted asymmetrically by pulling one end of the traction thread more than the other. Once the desired conformation of the valve is achieved, the ends of the traction thread are tied off. Massana's device is described in Cardiovascular Surgery 1980, a publication of Springer-Verlag Berlin Heidelberg.

Unfortunately, the totally flexible ring of Duran et al. and the totally flexible ring as modified by Massana, both fail to restore normal heart valve function. As discussed above, the most common heart valve defect is a dilatation of the posterior two-thirds of the valve annulus and an accompanying loss of normal configuration of the valve. Thus, the natural tendency of the damaged valve is to assume an unnatural shape. The rings of Duran et al. and Massana are unsatisfactory because they allow too much movement of the valve annulus, and the "normal" movement of a dilatated annulus is away from proper function.

Thus, it would be a significant contribution to the art of atrioventricular annuloplasty to provide a valve prosthesis that allows desirable anatomical movements of the annulus during the cardiac cycle, yet maintains a damaged annulus in the proper physiological shape to insure proper functioning of the valve.

BRIEF SUMMARY AND OBJECTS OF THE INVENTION

The present invention is directed to an atrioventricular annuloplasty prosthesis which has the desirable characteristics of allowing normal movement of the annulus during the cardiac cycle, yet provides sufficient support to maintain a damaged annulus in the proper anatomical shape for proper valve function. It also has the extremely significant advantage of being modifiable in its annular shape so that the prosthesis can be conformed to the desired shape of the annulus while it is being sutured into place.

This is accomplished by providing a biocompatible sheath or ring that is provided with a dynamic stiffener element situated within the sheath and having reciprocating characteristics which permit the stiffener element to be conformed to the desired shape of the annulus, and to follow limited movements of the valve annulus during the cardiac cycle.

It is, therefore, a primary object of the present invention to provide an improved heart valve prosthesis.

Another important object is to provide a valve prosthesis having characteristics allowing proper valve function while at the same time serving to maintain the valve in proper anatomical conformation.

These and other objects and features of the present invention will become more fully apparent from the following description and appended claims taken in conjunction with the accompanying drawing.

DETAILED DESCRIPTION OF THE PREFERRED EMBODIMENT

The present invention is directed to an atrioventricular annuloplasty prosthesis used to shape and support an atrioventricular valve annulus so as to restore proper valve function. At the same time, the apparatus of the invention allows for normal dynamic movement of the valve annulus during the cardiac cycle.

As seen above, it would be very desirable to have an atrioventricular annuloplasty prosthesis capable of restoring a damaged valve to normal function. Inasmuch as the mitral valve is far more likely to require repair than the tricuspid valve, the discussion herein will be directed to the repair of a mitral valve. However, it is to be understood that the same principles discussed in connection with the repair of a mitral valve are applicable to the repair of a tricuspid valve.

Figure 1:
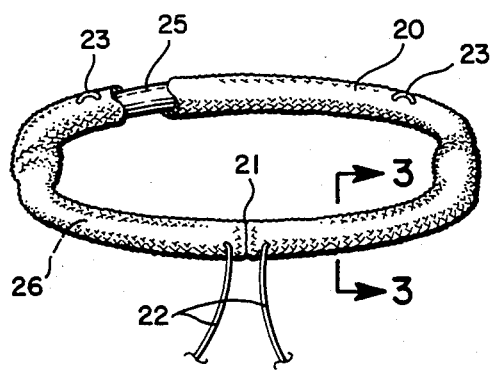
FIG. 1 is a perspective view of the prosthetic device of the present invention, with a portion of the sheath broken away to show the presence of one of the stiffener members.
Figure 3:
FIG. 3 is a cross-sectional view of the device taken along the line 3—3 of FIG. 1.

As shown in FIG. 1, one presently preferred embodiment of the present invention has a sheath 20, which may be formed by joining the ends of a length of tubular sheath material as at 21, so as to form a closed loop or ring. The sheath may be made of any suitable biocompatible material, such as described for example in U.S. Pat. No. 4,164,046, which is incorporated herein by reference. In order to provide for adjustment, a traction thread 22 is passed through the interior (see also FIG. 3) of the sheath 20 in a manner such that both ends of the thread 22 emerge from the closed loop in close proximity to one another so as to act like purse strings. In order to better anchor the traction thread 22 within the sheath 20, it may be desirable to pass thread 22 through sheath 20 at one or more locations as shown at 23.

Figure 4:
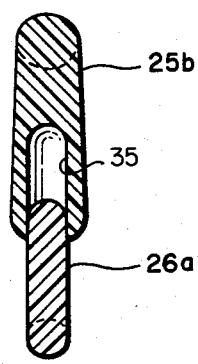
FIG. 4 is a longitudinal sectional view of one of the telescoping ends of the stiffener element taken along the line 4—4 of FIG. 2.
Figure 5:
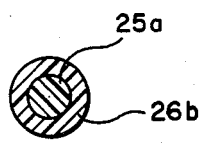
FIG. 5 is a cross-sectional view of one of the telescoping ends of the stiffener element taken along the line 5—5 of FIG. 2.

In the preferred embodiment, a dynamic stiffener element 24 (see FIG. 2) is situated within sheath 20. Stiffener element 24 is formed from two substantially identical stiffener members 25 and 26 shaped so that when fitted together, the stiffener element may be conformed to the desired shape of a valve annulus. Each stiffener member 25 and 26 is formed such that one of its ends 25a and 26a, respectively, is adapted to be inserted (see also FIGS. 4 and 5) into a corresponding end 26b, 25b of the other stiffener member in a telescoping fashion. For this purpose an interior bore 35 (see FIG. 4) is provided in the enlarged ends 25b, 26b so as to slidably receive the mating ends 26a, 25a.

Alternatively, the same type of telescoping fit may be achieved by using one stiffener member having both ends provided with an interior bore 35, and a second stiffener member having both ends adapted to engage the interior bore in telescopic fashion. However, it is more advantageous from a manufacturing point of view to make the two stiffener members 25, 26 identical so that a single mold can be used.

The circumference of sheath 20 should be such that the ends of stiffener members 25 and 26 will not become disengaged once they are enclosed in the sheath 20. The sheath should be constructed from a suitable material so that the telescoping action of the stiffener members is not impeded. Thus, sheath 20 is preferably formed from a material having a relatively loose weave so as to be flexible and compressible, and also biocompatible.

Figure 2:
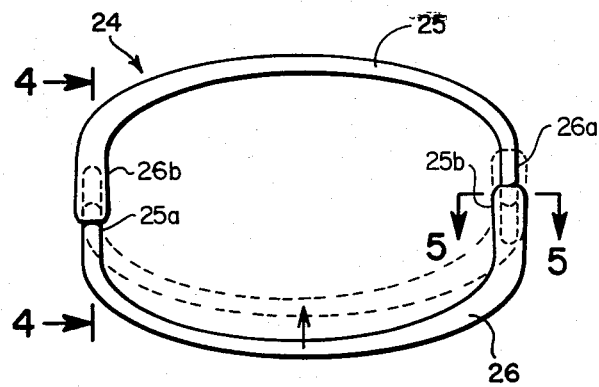
FIG. 2 is a plan view of the two stiffener members forming the stiffener element, with the telescopic adjustment being indicated in dashed lines.

When a stiffener element is formed of two stiffener members 25 and 26 in the manner shown in FIG. 2, the stiffener members may be made from a rigid or semirigid material such as stainless steel or plastic, thus providing adequate support to the valve annulus so as to insure that it maintains its proper physiological shape. At the same time, the reciprocating movement provided by the telescoping ends of the stiffener members 25 and 26 allows the annulus to undergo desirable anatomical movement during the cardiac cycle. Thus, when the prosthesis is implanted with the telescoping ends of members 25, 26 adjacent to the commissure of a mitral valve, the annulus will be permitted to undergo desirable physiological movement during the cardiac cycle, while being adequately supported so as to insure that it maintains the proper physiological configuration for the valve leaflets.

Figure 6:
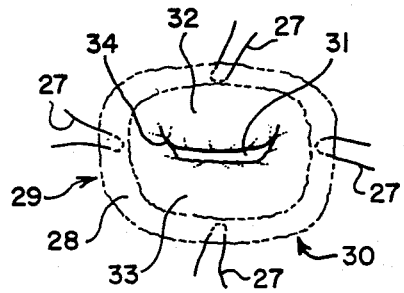
FIG. 6 is a schematic representation of a mitral valve showing four stay sutures placed around the circumference of the valve annulus.
Figure 7:
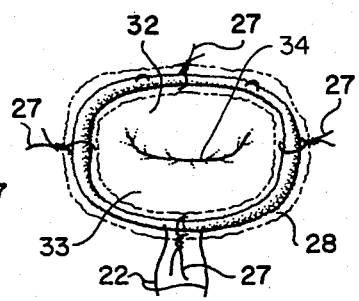
FIG. 7 is a schematic representation showing the prosthetic device of the present invention held in place by the four stay sutures.
Figure 8:
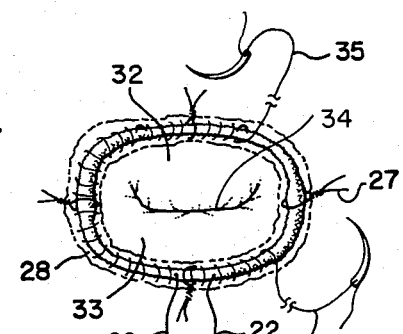
FIG. 8 is a schematic representation of the prosthetic device being secured to the valve annulus by a continuous suture.

FIGS. 6–8 are schematic representations of the various steps involved in implanting the prosthetic device of the present invention. FIG. 6 depicts the placement of several stay sutures 27 around the circumference of the annulus 28 of a mitral valve 29. The orientation of FIG. 6 is such that the top of the figure corresponds to the anterior portion of the annulus which is anchored to the aortic root. Thus, the lower portion of the figure corresponds to the section of the annulus that is typically dilatated in a damaged mitral valve, as indicated by a somewhat misshapen annulus as shown at 30, and a gap 31 caused by a poor fit of anterior leaflet 32 and posterior leaflet 33. The gap 31 thus permits regurgitation of blood from the ventricle into the atrium during contraction of the ventricle.

As shown in FIG. 7, the prosthetic device of the present invention is held in place on the annulus by tying the stay sutures 27. This step serves to bring the annulus 28 of the damaged valve roughly to the desired shape, and holds the prosthesis in approximately the proper position, thus making it easier to secure the device by a continuous suture, as illustrated at 35 in FIG. 8. Inasmuch as the posterior portion of the valve annulus is the portion needing reshaping, and since normal movement of the annulus occurs primarily adjacent to the commissure 34 in a mitral valve, the telescoping ends of stiffener members 25 and 26 are preferably located adjacent the opposite ends of the commissure 34. Since the annulus 28 is somewhat elliptical in shape, the location of the telescoping ends of stiffener members 25, 26 substantially corresponds to the points on the valve annulus 28 crossed by the major axis of the ellipse.

After the prosthesis has been secured in place by the stay sutures 27, it is securely affixed to the valve annulus 28 by use of a continuous suture 35 as illustrated in FIG. 8. The preferred method is to pass each suture around, rather than through, the sheath 20 in the manner shown so as to avoid binding the traction thread 22. It is advantageous to contract the prosthesis while placing the continuous suture so that the valve leaflets 32 and 33 are brought into substantial anatomical alignment at the commissure 34.

The use of a continuous suture 35 is advantageous because this type of suture tends to maintain the prosthesis in its partially contracted position. If individual sutures were used, the device would be free to assume its maximally extended shape, although as will be seen, the traction thread will overcome this latter problem where it is desired to use individual sutures.

An advantage of contracting the prosthectic device during implantation is that it allows the sutures to be placed in the annulus and around the prosthesis in a manner which will minimize stress on the sutures. If the dilatated annulus is secured to the prosthesis while in its extended configuration, there will be some "puckering" of the annulus between sutures after the device is contracted, thus resulting in unnecessary stress on the sutures at those points. This stress will be more evenly distributed if the dilatated annulus is forced to assume its contracted position as the sutures are placed.

Since the anterior portion of the annulus 28 is anchored to the aortic root, and since it is typically the posterior portion of the annulus that becomes dilatated, it may be convenient to commence the continuous suture 35 at the anterior portion of the annulus 28.

It is clear that implantation in the manner described will result in conformation of the annulus 28 to the shape of the prosthesis. Thus, because there is some natural variation in the sizes of normal atrioventricular heart valve annuli, it may be desirable to provide the prosthesis in more than one size. However, the fact that the device is modifiable in annular shape by means of the telescopic action provided at the ends of the stiffener members 25 and 26 means that the same type of prosthesis may be used on various patients having different valve annuli configurations.

Figure 9:
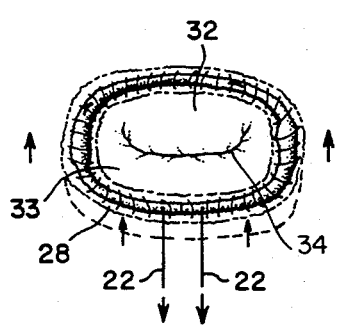
FIG. 9 is a schematic representation of symmetrical adjustment of the prosthetic device by pulling equally on both ends of a traction thread.
Figure 10:
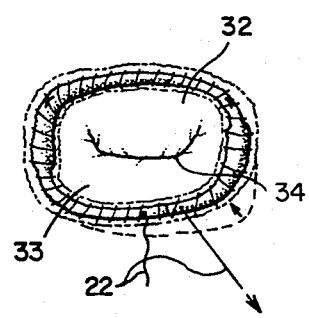
FIG. 10 is a schematic representation of asymmetrical adjustment of the prosthetic device by pulling on only the right end of a traction thread.
Figure 11:
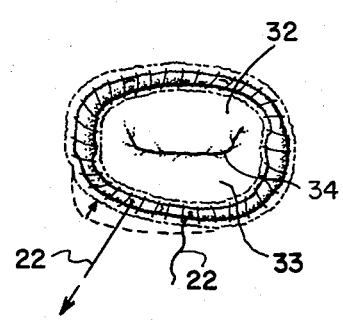
FIG. 11 is a schematic representation of asymmetrical adjustment of the prosthetic device by pulling on only the left end of a traction thread.

After the device has been implanted, it is possible to make final adjustments in the orientation of the valve leaflets 32 and 33 and the valve commissure 34 by tightening the traction thread 22, as shown in exaggerated fashion in FIGS. 9–11.

Thus, as shown in FIG. 9, if both ends of the traction thread 22 are pulled together, the sheath 20 and stiffener element 24 will be contracted symmetrically. On the other hand, as shown in FIGS. 10 and 11, if one end is pulled more than the other, the prosthesis will be contracted asymmetrically. Once the desired contraction has been achieved so as to bring the leaflets of the valve back into optimum anatomical alignment, the orientation of the prosthesis may be retained by typing off the ends of traction thread 22.

It should be understood that only a very limited range of adjustment of the prosthesis is required. Thus, a total range of contraction of three to four millimeters is all that is normally contemplated, and even less would be required for most applications. The degree of dynamic movement needed during the cardiac cycle would be an even smaller amount. Thus, as indicated above, FIGS. 10 and 11 have been exaggerated for purposes of illustration, and it is expected that most adjustments in the shape of the damaged valve can be accomplished with only a very slight, if any, amount of asymmetric contraction of the device. In cases where such adjustment is not necessary, it may be desirable to tie the ends of the traction thread so as to leave a small amount of play in order to allow a greater degree of dynamic movement of the stiffener members and the valve annulus during the cardiac cycle.

Although it has been shown how a traction thread may be advantageously used for finally adjusting the anatomical orientation of the valve leaflets or to limit the dynamic movement of the annulus, it should be understood that use of a traction thread is not required. Thus, when no traction thread is provided, the proper amount of contraction of the prosthesis can be achieved during placement of the continuous suture and the suture itself will provide a limit to the dynamic movement of the annulus.

After implantation, a heart valve supported by a prosthesis constructed according to the present invention will be forced to assume the shape of the partially contracted stiffener element. Yet, due to the reciprocating movement permitted by the telescoping ends of the stiffener members, it is possible for the device to undergo limited movement so as to allow desirable movement of the valve annulus during the cardiac cycle. Thus, despite the fact that the traction thread and continuous suture tend to maintain the prosthesis in its optimal shape so as to insure a proper physiological alignment of the valve leaflets during contraction of the ventricle, there is sufficient elasticity that the annulus can expand slightly against the influence of the sutures and traction thread. Of course, the device is not restrained from further contraction except by the forces required to further compress the annulus.

It can be seen that the choice of materials and the construction of the telescoping portions of the stiffener members are matters of design choice selected so that a sufficient range of contraction is available to allow the prosthesis to be used with a variety of sizes of valve annuli.

It can also be seen that when the device is contracted asymmetrically as shown in FIGS. 10 and 11, the stiffener members must not bind so as to defeat the dynamic action of the device. Thus, it may be desirable to taper ends 25a and 26a, or to enlarge the bore 27 (see FIG. 4) within the ends 25b and 26b, respectively. Alternatively, it may be desirable to construct the stiffener members 25, 26 from a material that is easily bendable and retains the bent shape so as to allow maximum freedom in conforming the device for optimum physiological operation in a particular patient. If a bendable type of material is used, even when the device is contracted asymmetrically, the ends of the stiffener members may be bent slightly in order to keep the telescoping portions in acceptable alignment.

Of course, it is to be understood that the present invention may be embodied in forms other than those specifically described herein without departing from the spirit or essential characteristics thereof. Thus, the described embodiments are to be considered in all respects only as illustrative and not restrictive and the scope of the invention is indicated by the appended claims rather than the foregoing description. All changes which come within the meaning and range of equivalence of the claims are to be embraced within this scope.

What is claimed and desired to be secured by United States Letters Patent is:

1. An atrioventricular annuloplasty prosthesis for use in repairing the annulus of a natural heart valve, comprising:

first means for providing a flexible, biocompatible material which may be sutured onto the annulus of a natural heart valve; and second means for stiffening essentially the entire circumference of said first means said second means being essentially rigid and having a generally oval-shaped configuration which substantially conforms to the shape of a normal heart valve annulus, and said stiffening means comprising two stiffener members secured together so as to allow reciprocating movement therebetween for permitting substantially rectilinear adjustment of the shape thereof at longitudinal ends of said oval configuration substantially adjacent to the positions where adjacent heart valve leaflets connect with the valve annulus so that rectilinear adjustment of the shape of the second means will cause the valve annulus of a natural heart valve to which the prosthesis is secured to be conformed to a suitable shape for acceptable operation of said natural heart valve.

2. An atrioventricular annulopolasty prosthesis as defined in claim 1 wherein the two stiffener members are substantially identical, and one end of each stiffener member is slidably engaged with the opposite end of the other stiffener member.

3. An atrioventricular annuloplasty prosthesis as defined in claim 2 wherein the said one end of each stiffener member is slidably engaged with the opposite end of the other stiffener member in telescoping fashion.

4. An atrioventricular annulopolasty prosthesis as defined in claim 2 wherein the location of the areas of reciprocating movement substantially corresponds with the points on the valve annulus corresponding to the major axis of symmetry through the center of the annulus.

5. An atrioventricular annuloplasty prosthesis as defined in claim 1 wherein the range of adjustment is about three to four millimeters.

6. An atrioventricular annuloplasty prosthesis as defined in claim 1 wherein said first means comprises a sheath which encapsulates said second means.

7. An atrioventricular annuloplasty prosthesis as defined in claim 6, further comprising means for adjusting the shape of said sheat once the sheath has been sutured onto the said annulus.

8. An atrioventricular annuloplasty prosthesis as defined in claim 7 wherein the adjustment means further comprises a traction thread passed through the interior of the sheath in a manner such that both ends of said traction thread emerge from said sheath so as to permit either end to be pulled.

9. An atrioventricular annuloplasty prosthesis for use in repairing the annulus of a natural heart valve, comprising:

means for providing a flexible, biocompatible sheath which may be sutured onto the annulus of a natural heart valve;

means for stiffening said sheath, said stiffening means having a generally oval configuration corresponding substantially to a normal heart valve annulus and being essentially rigid and encapsulated by said sheath, and comprising at least first and second members telescopically joined at the ends thereof to permit rectilinear adjustment of said stiffening means at positions substantially adjacent to the longitudinal ends where adjacent heart valve leaflets connect with the valve annulus, whereby adjustment of the width of the stiffening means will cause the valve annulus to be conformed to a suitable shape for acceptable operation of said natural heart valve; and means for adjusting the shape of said sheath and the stiffening means enclosed by said sheath once the sheath has been sutured onto the said annulus.

10. An atrioventricular annuloplasty prosthesis as defined in claim 9 wherein said stiffening means comprises two stiffening members, each said stiffening member being slidably joined at the ends thereof to the other stiffening member so as to allow reciprocating movement therebetween.

11. An atrioventricular annuloplasty prosthesis as defined in claim 10 wherein said means for adjusting the shape of said sheath and said stiffening means further comprises a traction thread passed through the interior of the sheath in a manner such that both ends of said traction thead emerge from said sheath so as to permit either end thereof to be pulled.

12. An atrioventricular annuloplasty prosthesis as defined in claim 11 wherein the two stiffener members are substantially identical, and wherein one end of each stiffener member is slidably engaged with the opposite end of the other stiffener member.

13. An atrioventricular annuloplasty prosthesis as defined in claim 12 wherein the range of reciprocating movement between the said stiffening members is about three to four millimeters.

14. an atrioventricular annuloplasty prosthesis for use in repairing the annulus of a natural heart valve, comprising:

a sheath formed from flexible, biocompatible material which may be sutured onto the annulus of a natural heart valve;

a stiffening element encapsulated within said sheath, said stiffening element having a generally oval configuration corresponding substantially to a normal heart valve annulus, said stiffening element comprising two stiffening members, each said stiffening member being slidably joined at longitudinal ends of said oval configuration at a position substantially corresponding to the points corresponding to the major axis of symmetry through the center of said stiffening element so as to permit substantially rectilinear reciprocating movement therebetween for purposes of permitting adjustment of the width of the stiffening element so that such adjustment of the width of the stiffening element will cause the valve annulus of a natural heart valve to which the prosthesis is secured to be conformed to a suitable shape for acceptable operation of said natural heart valve; and a traction thread passed through the interior of the sheath in a manner such that both ends of said traction thread emerge from the said sheath so as to permit either end to be pulled for purposes of adjusting the shape of the sheath and stiffening element once the sheath has been sutured onto the annulus.

* * * * *

UNITED STATES PATENT AND TRADEMARK OFFICE
CERTIFICATE OF CORRECTION

PATENT NO. : 4,489,446
DATED : December 25, 1984
INVENTOR(S) : Charles C. Reed

It is certified that error appears in the above-identified patent and that said Letters Patent is hereby corrected as shown below:

Column 6, line 20, "typing" should be --tying--.

Signed and Sealed this

Twenty-first Day of May 1985

[SEAL]

Attest:

DONALD J. QUIGG

*Attesting Officer*   Acting Commissioner of Patents and Trademarks